US00PP13345P2

(12) United States Plant Patent
Utecht

(10) Patent No.: US PP13,345 P2
(45) Date of Patent: Dec. 10, 2002

(54) GERANIUM PLANT NAMED 'FISBILRED'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/800,498

(22) Filed: Mar. 8, 2001

(51) Int. Cl.[7] ..... A01H 5/00
(52) U.S. Cl. ..... Plt./332
(58) Field of Search ..... Plt./332

(56) References Cited

PUBLICATIONS

GTITM UPOVROM Citation for 'Fisbilred' as per QZ PBR 991260; Sep. 13, 1999.*
GTITM UPOVROM Citation for Fisbilred as per CA PBR 99–1884; Nov. 30, 1999.*
Fischer Website, New Geranium Varieties for 2000–2001.*
2001 Fischer Selections/Plant Alliance Catalogue featuring 'Fisbilred', p. 31.
Bulletin des Variétées Végétales, No. 42, Canadian Plant Breeders' Rights Office, January 2002.
Official Gazette of the Community Plant Variety Office, European Community, Dec. 15, 1999.

* cited by examiner

*Primary Examiner*—Kent L. Bell
(74) *Attorney, Agent, or Firm*—Foley & Lardner

(57) ABSTRACT

A new and distinct cultivar of geranium plant named 'Fisbilred', as described and illustrated, and particularly characterized by the combined features of red, double, bell-shaped flowers, rich flowering with compact, round umbels, medium green, distinctly ivy-shaped foliage, and medium-tall, bushy and round plant habit.

2 Drawing Sheets

LATIN NAME OF THE GENUS AND SPECIES OF THE PLANT CLAIMED

*Pelargonium peltatum* L'Héritier ex Aiton.

VARIETY DENOMINATION

'Fisbilred'.

BACKGROUND OF THE INVENTION

The present invention comprises a new and distinct cultivar of geranium, botanically known as *Pelargonium peltatum*, and hereinafter referred to by the cultivar name 'Fisbilred'.

'Fisbilred' is a product of a planned breeding program which had the objective of creating new ivy geranium cultivars with double flowers in combination with moderately vigorous growth and in various different colors.

'Fisbilred' originated from a hybridization made by the inventor Angelika Utecht in a controlled breeding program in Galdar, Gran Canaria, Spain, in 1995. The female parent was a hybrid seedling, No. 361-3 (unpatented), having intense red, double flowers, medium green foliage without zonation, and medium tall plant habit. The male parent of 'Fisbilred' was a self-seedling from the commercial variety 'Gauguin', synonym 'Nanatte', U.S. Plant Pat. No. 7,360, which was characterized by light-red, semi-double to double flowers, medium green foliage with weak zonation, and vigorous growth.

'Fisbilred' was selected as one flowering plant within the progeny of the stated cross by Angelika Ultecht in a controlled environment in Galdar, Gran Canaria, Spain, in 1996. The first act of asexual reproduction of 'Fisbilred' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from these cuttings initiated in the spring of 1997 in Hillscheid, Germany, and continuing thereafter, has demonstrated that the combination of characteristics as herein disclosed for 'Fisbilred' are firmly fixed and are retained through successive generations of asexual reproduction.

'Fisbilred' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fisbilred', which in combination distinguish this geranium as a new and distinct cultivar:

1. Red, many petaled, and rose-bud shaped flowers;
2. Numerous, relatively small, tight umbels;
3. Medium-green, distinctly lobed, and slightly zoned foliage;
4. Medium-sized, tight, round and well-branched plant habit; and
5. Early to medium spring flowering response.

Of the many commercial cultivars known to the present inventor, there is none that is very close to 'Fisbilred', it could, however, partly be compared with 'Fisbarock', U.S.

Plant Pat. No. 12,367. In comparison to 'Fisbarock', 'Fisbilred' has a brighter red flower color, partly white colored lower surface of petals, smaller and rose-bud shaped flowers, and more distinctly lobed foliage with weak zonation ('Fisbarock' has almost no zonation).

BRIEF DESCRIPTION OF THE DRAWING

The accompanying photographic drawings show typical flower and foliage characteristics of 'Fisbilred' with colors being as true as possible with illustrations of this type.

The photograph on sheet one depicts a typical plant of 'Fisbilred'.

The photograph on sheet 2 depicts a close up view of typical flowers and leaves of 'Fisbilred'.

DETAILED BOTANICAL DESCRIPTION

The measurements were taken in Langley, Canada, on Jul. 20, 2000. The plants were growing in 6 inch pots in a greenhouse, and had had 15 weeks of cultivation time from the planting of rooted cuttings on Apr. 3, 2000. The plants had not been pinched.

In the following description color references are made to The Royal Horticultural Society Colour Chart (R.H.S). The color values were determined indoors from plants developed in a greenhouse in May 2000, Hillscheid, Germany.

INFLORESCENCE

Lastingness of the bloom: Initial flower lasts about 9 days at 18° C., umbel lasts about 16 days.

Fragrance: None.

Umbel:

*Shape.*—Semi-spherical, relatively small and compact.

*Average diameter.*—80 mm.

*Average depth.*—45 mm.

*Peduncle length.*—118 mm.

*Peduncle color.*—Light green, RHS 143 C to 144 A, no anthocyanin.

*Pedicel length.*—17.5 mm, without spur.

*Pedicel color.*—Grass-green, about RHS 143 A.

*Number of flowers per umbel.*—Approximately 11–13.

Corolla:

*Average diameter.*—40 mm.

*Average depth.*—About 21–23 mm.

*Form.*—Double.

*Shape.*—Round, young flowers are rose-bud- or bell-shaped.

*Number of petals.*—38–40.

*Size.*—Outer petals are about 25–27 mm long and 14–16 mm wide; inner petals diminish in length but not in width.

*Shape.*—Outer petals are spatulate with attenuate base, upper end rounded; inner petals are obovate, with rounded tips and attenuate base; margins are mostly entire with occasional small notch at the tip of the petal.

*Color (general tonality from a distance of three meters)*.—Medium (true) red.

*Color of upper petals.*—RHS 46 B.

*Markings of upper petals.*—Weak dark-purple veins. RHS 187 B, not visible in the photograph.

*Color of lower petals.*—RHS 46 B.

*Color of lower surface of petals.*—RHS 46 B to 46 C (margin), center of petal whitish, RHS 49 D.

*Color of sepals.*—Upper surface grass-green, RHS 143 A; lower surface light green, RHS 143 C no anthocyanin.

*Size of sepals.*—Length 10–12 mm; width 4 mm for largest, upper sepal; 2–3 mm in width for other sepals.

*Shape of sepals.*—Linearis to lanceolate; acute tip; truncate base; surface with weak, short pubescence; margin entire.

*Number of sepals.*—6–8.

Bud: (just prior to petals unfolding):

*Shape.*—Nearly round, bell-shaped.

*Color (lower part — sepals).—Grass-green, RHS* 143 A.

*Color (upper part — petals).—Cream-colored, RHS* 49 D, with red margin RHS 46 C.

*Length.*—17 mm.

*Width.*—13 mm.

Reproductive organs:

*Androecium.*—No anthers, no pollen.

*Gynoecium.*—No pistil observed.

*Fertility/seed set.*—None observed to date.

Spring flowering response period: In Hillscheid, Germany, in 2000, plants had on average 1.0 flowers opened 12 weeks after planting of rooted cuttings (pinched plants).

Outdoor flower production: Rich and continuously flowering, the flower count in Hillscheid, Germany, indicated about 6–7 inflorescence per plant in mid-May.

Durability: Good shatter resistance, rain resistance fair for this type of flower (dense, multi-petaled), good stability of flower color.

Pest/disease resistance/susceptibility: Relatively good tolerance to botrytis.

PLANT

Foliage:

*Shape.*—Ivy-shaped with distinct lobes with rounded tips, with cordate shaped base.

*Margin.*—Mainly entire, single notches near the tips of lobes.

*Texture.*—Slightly glossy surface.

*Size of leaf.*—89 mm wide, 55 mm long.

*Color of upper surface.*—Medium green, approximately RHS137 B.

*Color of lower surface.*—Near RHS 137 D.

*Petioles.*—50–60 mm long; 2–3 mm diameter; color about RHS 143 C.

*Color of zonation.*—Brown, RHS 166 A, forming a weak, narrow ring.

General appearance and form:

*Internode length.*—30–35 mm.

*Branching pattern.*—6.5 branches.

*Length of branches.*—47.2 cm for 15 week old plants in Langley, Canada, about 85 cm in mid-September in Hillscheid, Germany 31 weeks old (branches measured from the soil level to the tips of the branches without inflorescences).

I claim:

1. A new and distinct cultivar of geranium plant named 'Fisbilred', as described and illustrated.

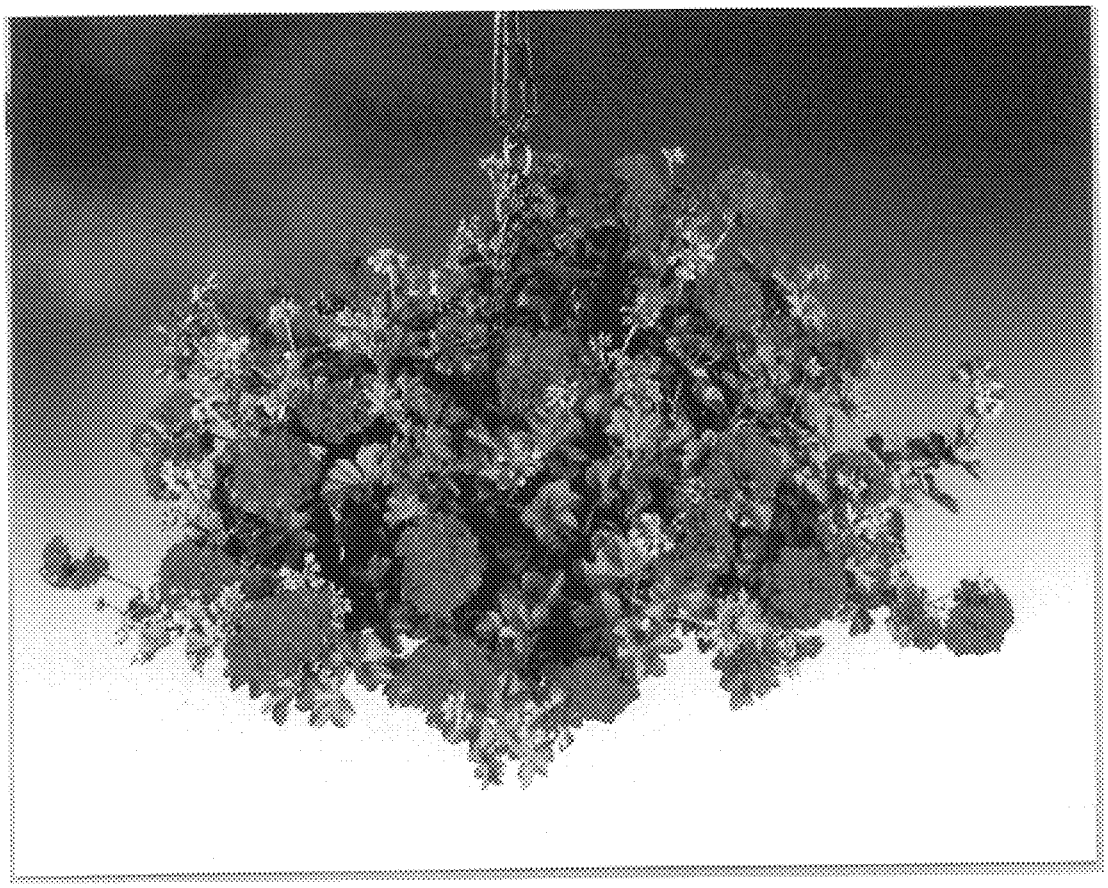

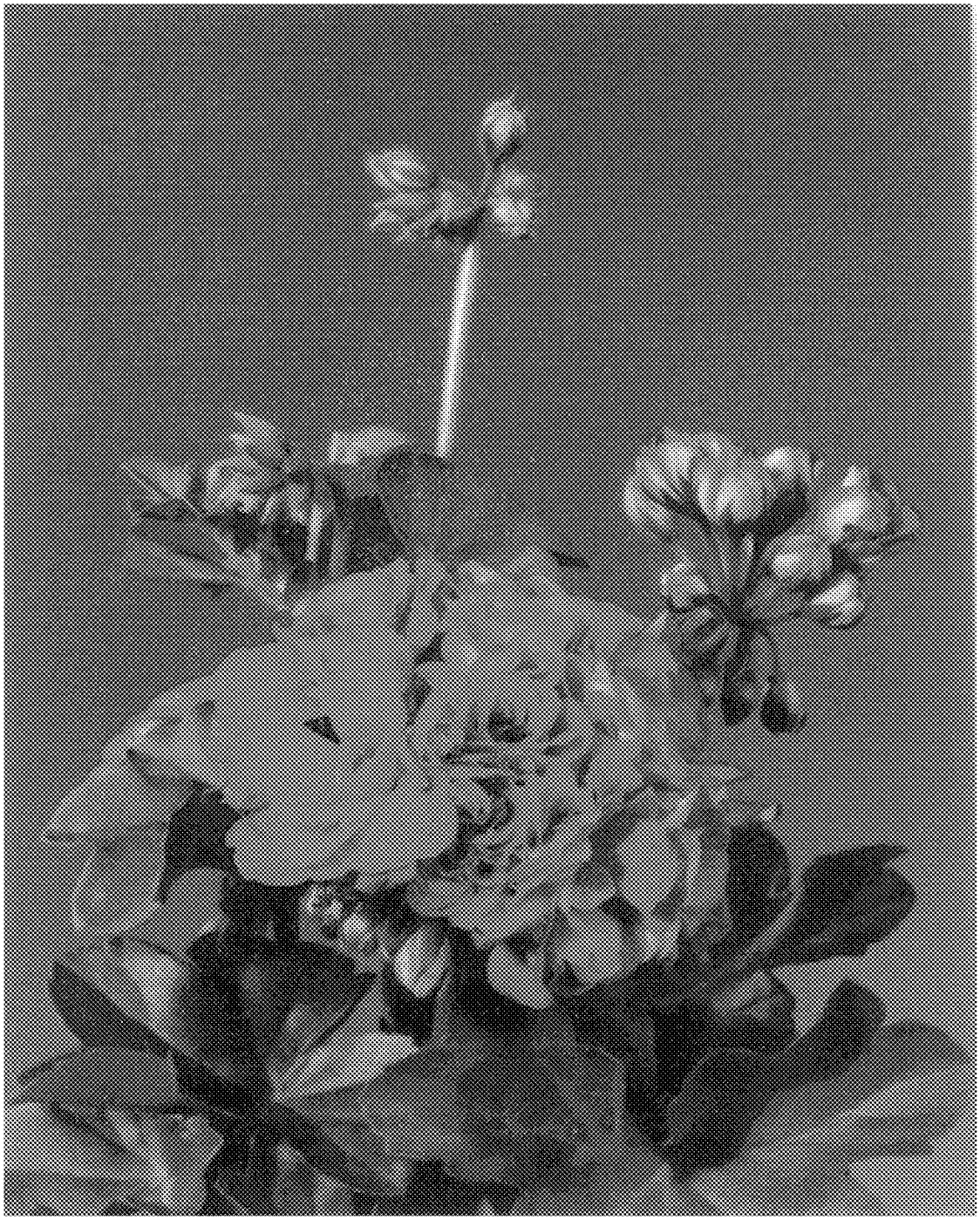

* * * * *